(12) United States Patent
Shibayama et al.

(10) Patent No.: US 9,863,884 B2
(45) Date of Patent: *Jan. 9, 2018

(54) SURFACE-ENHANCED RAMAN SCATTERING ELEMENT, AND METHOD FOR PRODUCING SAME

(71) Applicant: HAMAMATSU PHOTONICS K.K., Hamamatsu-shi, Shizuoka (JP)

(72) Inventors: Katsumi Shibayama, Hamamatsu (JP); Masashi Ito, Hamamatsu (JP); Takafumi Yokino, Hamamatsu (JP); Masaki Hirose, Hamamatsu (JP); Anna Yoshida, Hamamatsu (JP); Kazuto Ofuji, Hamamatsu (JP); Yoshihiro Maruyama, Hamamatsu (JP); Takashi Kasahara, Hamamatsu (JP); Toshimitsu Kawai, Hamamatsu (JP); Toru Hirohata, Hamamatsu (JP); Hiroki Kamei, Hamamatsu (JP); Hiroki Oyama, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/420,510

(22) PCT Filed: Aug. 9, 2013

(86) PCT No.: PCT/JP2013/071707
§ 371 (c)(1),
(2) Date: Feb. 9, 2015

(87) PCT Pub. No.: WO2014/025037
PCT Pub. Date: Feb. 13, 2014

(65) Prior Publication Data
US 2015/0219562 A1 Aug. 6, 2015

(30) Foreign Application Priority Data

Aug. 10, 2012 (JP) .................................. 2012-178763
Aug. 10, 2012 (JP) .................................. 2012-178765

(Continued)

(51) Int. Cl.
*G01N 21/65* (2006.01)
*G01N 21/03* (2006.01)
*B82Y 40/00* (2011.01)

(52) U.S. Cl.
CPC ........... *G01N 21/658* (2013.01); *G01N 21/03* (2013.01); *B82Y 40/00* (2013.01); *G01N 2021/651* (2013.01)

(58) Field of Classification Search
CPC . G01N 21/03; G01N 21/658; G01N 2021/651
See application file for complete search history.

(56) References Cited

U.S. PATENT DOCUMENTS

| 4,589,551 A | 5/1986 | Hellon |
| 5,090,568 A | 2/1992 | Tse |

(Continued)

FOREIGN PATENT DOCUMENTS

| CN | 1563989 | 1/2005 |
| CN | 1957245 | 5/2007 |

(Continued)

OTHER PUBLICATIONS

English Machine Translation of JP 2011-107032, Nishikawa et al., Jun. 2, 2011.*

(Continued)

*Primary Examiner* — Dominic J Bologna
(74) *Attorney, Agent, or Firm* — Drinker Biddle & Reath LLP

(57) ABSTRACT

A SERS element comprises a substrate having a front face; a fine structure part formed on the front face and having a (Continued)

plurality of pillars; and a conductor layer formed on the fine structure part and constituting an optical function part for generating surface-enhanced Raman scattering. The conductor layer has a base part formed along the front face and a plurality of protrusions protruding from the base part at respective positions corresponding to the pillars. The base part has a thickness greater than the height of the pillars.

5 Claims, 13 Drawing Sheets

(30) Foreign Application Priority Data

| Aug. 10, 2012 | (JP) | 2012-178766 |
|---|---|---|
| Aug. 10, 2012 | (JP) | 2012-178767 |
| Aug. 10, 2012 | (JP) | 2012-178768 |
| Aug. 10, 2012 | (JP) | 2012-178771 |
| Aug. 10, 2012 | (JP) | 2012-178773 |
| Aug. 10, 2012 | (JP) | 2012-178778 |
| Aug. 10, 2012 | (JP) | 2012-178976 |
| Mar. 29, 2013 | (JP) | 2013-073308 |
| Mar. 29, 2013 | (JP) | 2013-073312 |
| Mar. 29, 2013 | (JP) | 2013-073315 |
| Mar. 29, 2013 | (JP) | 2013-073444 |
| Jul. 5, 2013 | (JP) | 2013-142163 |

(56) References Cited

U.S. PATENT DOCUMENTS

| 5,655,661 | A | 8/1997 | Rigby |
|---|---|---|---|
| 5,772,905 | A | 6/1998 | Chou |
| 6,582,996 | B1 | 6/2003 | Hara et al. |
| 6,614,523 | B1 | 9/2003 | Boss et al. |
| 6,967,717 | B1 | 11/2005 | Boss et al. |
| 6,970,239 | B2 | 11/2005 | Chan et al. |
| 7,148,964 | B2 | 12/2006 | Cunningham et al. |
| 7,236,242 | B2 | 6/2007 | Kamins et al. |
| 7,428,046 | B2 | 9/2008 | Wang et al. |
| 7,460,224 | B2 | 12/2008 | Wang et al. |
| 7,483,130 | B2 | 1/2009 | Baumberg et al. |
| 7,545,490 | B1 | 6/2009 | Pendell-Jones |
| 7,876,425 | B2 | 1/2011 | Sardashti et al. |
| 8,416,406 | B2 | 4/2013 | Stuke et al. |
| 9,127,984 | B2 | 9/2015 | Tseng et al. |
| 9,267,894 | B2 | 2/2016 | Ito et al. |
| 2003/0059820 | A1 | 3/2003 | Vo-Dinh |
| 2003/0157732 | A1 | 8/2003 | Baker et al. |
| 2003/0235520 | A1 | 12/2003 | Shea et al. |
| 2004/0023046 | A1* | 2/2004 | Schlottig ............ G01J 3/44 428/469 |
| 2005/0224253 | A1 | 10/2005 | Aoki et al. |
| 2006/0034729 | A1 | 2/2006 | Poponin |
| 2006/0061762 | A1 | 3/2006 | Dwight et al. |
| 2006/0119250 | A1 | 6/2006 | Suehiro et al. |
| 2006/0146323 | A1 | 7/2006 | Bratkovski et al. |
| 2006/0164637 | A1 | 7/2006 | Wang |
| 2007/0015288 | A1 | 1/2007 | Hulteen et al. |
| 2007/0140900 | A1 | 6/2007 | Wang et al. |
| 2007/0145249 | A1 | 6/2007 | Kiesel et al. |
| 2007/0153267 | A1 | 7/2007 | Wang et al. |
| 2007/0254377 | A1 | 11/2007 | Li et al. |
| 2008/0073206 | A1 | 3/2008 | Nogawa |
| 2008/0094621 | A1 | 4/2008 | Li et al. |
| 2008/0142822 | A1 | 6/2008 | Kim et al. |
| 2008/0174775 | A1 | 7/2008 | Moskovits et al. |
| 2008/0218761 | A1 | 9/2008 | Nishikawa et al. |
| 2008/0297802 | A1 | 12/2008 | Ogawa et al. |
| 2009/0108181 | A1 | 4/2009 | Ishihara et al. |
| 2009/0137411 | A1 | 5/2009 | Sun et al. |
| 2009/0231586 | A1 | 9/2009 | Murakami et al. |
| 2010/0009456 | A1 | 1/2010 | Prins et al. |
| 2010/0019355 | A1 | 1/2010 | Kamins et al. |
| 2010/0078860 | A1 | 4/2010 | Yoneda et al. |
| 2010/0085566 | A1 | 4/2010 | Cunningham |
| 2010/0195106 | A1 | 8/2010 | Ogawa |
| 2010/0240144 | A1 | 9/2010 | Gilbert |
| 2010/0296086 | A1 | 11/2010 | Wang et al. |
| 2010/0321684 | A1 | 12/2010 | Bratkovski et al. |
| 2011/0027901 | A1 | 2/2011 | Gaster et al. |
| 2011/0096157 | A1 | 4/2011 | Fine et al. |
| 2011/0116089 | A1 | 5/2011 | Schmidt et al. |
| 2011/0166045 | A1* | 7/2011 | Dhawan ............... B82Y 10/00 506/39 |
| 2011/0194116 | A1 | 8/2011 | Horiuchi et al. |
| 2011/0267607 | A1 | 11/2011 | Hu et al. |
| 2011/0267608 | A1 | 11/2011 | Ou et al. |
| 2011/0300691 | A1 | 12/2011 | Sakamoto et al. |
| 2011/0317160 | A1 | 12/2011 | Li et al. |
| 2012/0081703 | A1 | 4/2012 | Moskovits et al. |
| 2012/0086021 | A1 | 4/2012 | Wang |
| 2012/0105841 | A1 | 5/2012 | Hu et al. |
| 2012/0162640 | A1 | 6/2012 | Sakagami |
| 2012/0170033 | A1 | 7/2012 | Zhu et al. |
| 2012/0182548 | A1 | 7/2012 | Harb et al. |
| 2012/0265038 | A1 | 10/2012 | Kawamura et al. |
| 2013/0142987 | A1 | 6/2013 | Wardle et al. |
| 2013/0176562 | A1 | 7/2013 | Shioi et al. |
| 2013/0252275 | A1 | 9/2013 | Tokonami et al. |
| 2014/0028995 | A1 | 1/2014 | Bratkovski et al. |
| 2014/0043605 | A1 | 2/2014 | Tseng et al. |
| 2014/0045209 | A1 | 2/2014 | Chou et al. |
| 2014/0154668 | A1 | 6/2014 | Chou et al. |
| 2014/0218727 | A1 | 8/2014 | Li et al. |
| 2014/0347661 | A1 | 11/2014 | Kim et al. |
| 2015/0204792 | A1 | 7/2015 | Shibayama et al. |
| 2015/0211999 | A1 | 7/2015 | Maruyama et al. |
| 2015/0212000 | A1 | 7/2015 | Maruyama et al. |
| 2015/0212002 | A1 | 7/2015 | Ito et al. |
| 2015/0212003 | A1 | 7/2015 | Shibayama et al. |
| 2015/0219562 | A1 | 8/2015 | Shibayama et al. |
| 2015/0233832 | A1 | 8/2015 | Maruyama et al. |
| 2015/0233833 | A1 | 8/2015 | Shibayama et al. |
| 2015/0338346 | A1 | 11/2015 | Chou et al. |
| 2016/0061736 | A1 | 3/2016 | Ito et al. |
| 2016/0146736 | A1 | 5/2016 | Chen et al. |

FOREIGN PATENT DOCUMENTS

| CN | 101024483 | 8/2007 |
|---|---|---|
| CN | 101057132 | 10/2007 |
| CN | 101223435 | 7/2008 |
| CN | 101281133 | 10/2008 |
| CN | 101400976 | 4/2009 |
| CN | 101408513 | 4/2009 |
| CN | 101460830 | 6/2009 |
| CN | 101490535 | 7/2009 |
| CN | 101523212 | 9/2009 |
| CN | 101529229 | 9/2009 |
| CN | 101566571 | 10/2009 |
| CN | 101629906 | 1/2010 |
| CN | 101672784 | 3/2010 |
| CN | 101680900 | 3/2010 |
| CN | 101910829 | 12/2010 |
| CN | 101936906 | 1/2011 |
| CN | 102016585 | 4/2011 |
| CN | 102072878 | 5/2011 |
| CN | 102103086 | 6/2011 |
| CN | 102169086 | 8/2011 |
| CN | 102169088 | 8/2011 |
| CN | 102282094 | 12/2011 |
| CN | 102307699 | 1/2012 |
| CN | 102330080 | 1/2012 |
| CN | 102348966 | 2/2012 |
| CN | 102482665 | 5/2012 |
| CN | 102483354 | 5/2012 |
| CN | 102483866 | 5/2012 |
| CN | 102590088 | 7/2012 |
| CN | 102713720 | 10/2012 |
| CN | 103930780 | 7/2014 |
| CN | 104011520 | 8/2014 |

(56) References Cited

FOREIGN PATENT DOCUMENTS

| | | |
|---|---|---|
| EP | 1374989 | 1/2004 |
| EP | 2101166 | 9/2009 |
| EP | 2278301 | 1/2011 |
| EP | 2352010 | 8/2011 |
| EP | 2386847 | 11/2011 |
| EP | 2469598 | 6/2012 |
| GB | 2419940 | 5/2006 |
| JP | S56-142454 | 10/1981 |
| JP | H05-044867 U | 6/1993 |
| JP | H07-260646 A | 10/1995 |
| JP | 2003-026232 A | 1/2003 |
| JP | 2003-240705 | 8/2003 |
| JP | 2005-337771 A | 12/2005 |
| JP | 2006-208271 | 8/2006 |
| JP | 2006-250924 | 9/2006 |
| JP | 2007-530925 A | 11/2007 |
| JP | 2007-538264 A | 12/2007 |
| JP | 2008-064574 | 3/2008 |
| JP | 2008-128786 | 6/2008 |
| JP | 2008-519254 A | 6/2008 |
| JP | 2008-196992 A | 8/2008 |
| JP | 2008-268059 A | 11/2008 |
| JP | CN 101319994 | 12/2008 |
| JP | 2009-025316 A | 2/2009 |
| JP | 2009-047623 A | 3/2009 |
| JP | 2009-103643 A | 5/2009 |
| JP | 2009-222507 A | 10/2009 |
| JP | 2009-236830 A | 10/2009 |
| JP | 2009-544967 A | 12/2009 |
| JP | 2010-506191 A | 2/2010 |
| JP | 2010-230352 | 10/2010 |
| JP | 2011-021085 | 2/2011 |
| JP | 2011-033518 A | 2/2011 |
| JP | 2011-506916 A | 3/2011 |
| JP | 2011-075348 A | 4/2011 |
| JP | 2011-107032 A | 6/2011 |
| JP | 2011-141264 | 7/2011 |
| JP | 2011-141265 A | 7/2011 |
| JP | 2011-201769 | 10/2011 |
| JP | 2011-215021 A | 10/2011 |
| JP | 2012-063293 | 3/2012 |
| JP | 2012-233707 A | 11/2012 |
| JP | 2013-173444 | 9/2013 |
| JP | 2012-508881 | 2/2014 |
| JP | 2014-037969 | 2/2014 |
| JP | 2014-196974 | 10/2014 |
| JP | 2014-196981 | 10/2014 |
| JP | 5779963 | 9/2015 |
| TW | 200728706 | 8/2007 |
| TW | 200932913 | 8/2009 |
| TW | 201111771 | 4/2011 |
| TW | 201410591 | 3/2014 |
| WO | WO 2002-004951 | 1/2002 |
| WO | WO 2006/138442 | 12/2006 |
| WO | WO-2007/149120 A2 | 12/2007 |
| WO | WO 2008/030666 | 3/2008 |
| WO | WO 2010/033267 | 3/2010 |
| WO | WO-2010/050203 A1 | 5/2010 |
| WO | WO-2010/090111 A1 | 8/2010 |
| WO | WO 2010/104520 | 9/2010 |
| WO | WO-2011/021085 A2 | 2/2011 |
| WO | WO 2011/022093 | 2/2011 |
| WO | WO-2011/040504 A1 | 4/2011 |
| WO | WO 2011/047199 | 4/2011 |
| WO | WO 2011/121857 | 10/2011 |
| WO | WO-2012/024006 A2 | 2/2012 |
| WO | WO 2012/077756 | 6/2012 |
| WO | WO 2013/015810 | 1/2013 |
| WO | WO 2013/058739 | 4/2013 |
| WO | WO 2013/062540 | 5/2013 |
| WO | WO-2014/025033 A1 | 2/2014 |
| WO | WO-2014/025034 A1 | 2/2014 |
| WO | WO 2014/156329 | 10/2014 |

OTHER PUBLICATIONS

W. Zhang et al,, "Giant and uniform fluorescence enhancement over large areas using plamonic nanodots in 3D resonant cavity nanoantenna by nanoimprinting", Nanotechnolgy, vol. 23, No. 22, May 10, 2012, p. 225301, XP020224099.

S. M. Wells et al., "Efficient disc on pillar substrates for surface enhanced Raman spectroscopy", Chemical Communications—Chemcom, vol. 47, No. 13, Jan. 1, 2011, p. 3814-p. 3816, XP055289549.

U.S. Office Action dated Oct. 19, 2015 that issued in U.S. Appl. No. 14/420,483 including Double Patenting Rejections on pp. 13-15.

Di Zhi-gang et al., "Simulation and optimization of SERS effect in nana Ag substrates", Laser & Infrared, vol. 41, No. 8, Aug. 31, 2011, p. 850-p. 855.

W. Wu et al., "Rational engineering of highly sensitive SERS substrate based on nanocone structures", Proceedings of SPIE, vol. 7673, Apr. 23, 2010, p. 767300-p. 767300-6, XP055172245.

Zhida Xu et al., "Nanoreplicated positive and inverted submicrometer polymer pyramid array for surface-enchanced Rama spectroscopy," Journale of Nanophotonics, vol. 5, No. 1, Jan. 1, 2011, p. 053526, XP055284283.

Hiroshi Hiroshima et al., "Homogeneity of Residual Layer thickness in UV Nanoimprint Lithography" Japanese Journal of Applied Physics, Jun. 1, 2009, p. 6-p. 18, XP55284163.

Liu Gang et al., "Nanowell surface enhanced Raman scattering arrays fabricated by soft-lithography for label-free biomolecular detections in integrated microfluidics," Applied Physics Letters, vol. 87, No. 7, Aug. 11, 2005, p. 71101, XP012077510.

English-language translation of International Preliminary Report on Patentability (IPRP) dated Oct. 8, 2015 that issued in WO Patent Application No. PCT/JP2014/052926.

English-language translation of International Preliminary Report on Patentability (IPRP) dated Oct. 8, 2015 that issued in WO Patent Application No. PCT/JP2014/052927.

English-language translation of International Preliminary Report on Patentability (IPRP) dated Oct. 8, 2015 that issued in WO Patent Application No. PCT/JP2014/052928.

K. Nakamoto et al., "Arrays of Metallic Nanopillars in Holes for Plasmonic Devices", Retrieved from the Internet: URL: http://www.rsc.org/images/LOC/2011/PDFs/Papers/596_0021.pdf, Oct. 6, 2011, XP055289892.

M. Tomohiko et al., "New localized surface plasmon resonance sensor utilizing nanoimprinting technology", NSTI Nanotechnology Conference and Trade Show—NSTI Nanotech, vol. 1, May 11, 2006, p. 58-p. 61, XP009098538.

W. D. Li et al., "Three-dimensional cavity nanoantenna coupled plasmonic nanodots for ultrahigh and uniform surface-enhanced Raman scattering over large area", Optics Express, vol. 19, No. 5, Feb. 14, 2011, p. 3925-3936, XP002751299.

U.S. Office Action dated Dec. 10, 2015 that issued in U.S. Appl. No. 14/420,404 including Double Patenting Rejections on pp. 12-15.

U.S. Office Action dated Dec. 14, 2015 that issued in U.S. Appl. No. 14/420,422 including Double Patenting Rejections on pp. 8-11.

Wei Fen Jiang et al., "Improved surface-enchanced Raman scattering of patterned gold nanoparticles deposited on silicon nanoporous pillar arrays", Applied Surface Science, vol. 257, No. 18, Apr. 25, 2011, p. 8089-p. 8092, XP028373693.

Su Yeon Lee, et al., "Freestanding and Arrayed Nanoporous Microcylinders for Highly Active 3D SERS Substrate", Chemistry of Materials, vol. 25, No. 12, Jun. 25, 2013, p. 2421-p. 2426, XP55286875.

"Q-SERS™ G1 Substrate," Opto Science, Inc. (retrieved on-line on Jul. 5, 2013).

Masahiro Yanagisawa, "Detection of Trace Organic Gas Using Molecular Sensor with Plasmon Antenna," Green Technology, Vo. 22, No. 6, Jun. 10, 2012, pp. 42-47, including at least partial English-language translation.

Zhiqiang Sun et al., "Fabricating Ordered Microstructures on the Basis of Self-assembled Colloidal Crystals", Major: Polymer Chemistry and Physics, vol. 8, Aug. 15, 2009, p. B014-p. 158.

(56) References Cited

OTHER PUBLICATIONS

U.S. Office Action dated Jun. 9, 2017 that issued in U.S. Appl. No. 14/780,776 including Double Patenting Rejections on pp. 8-10.

* cited by examiner

Fig.7
(a) 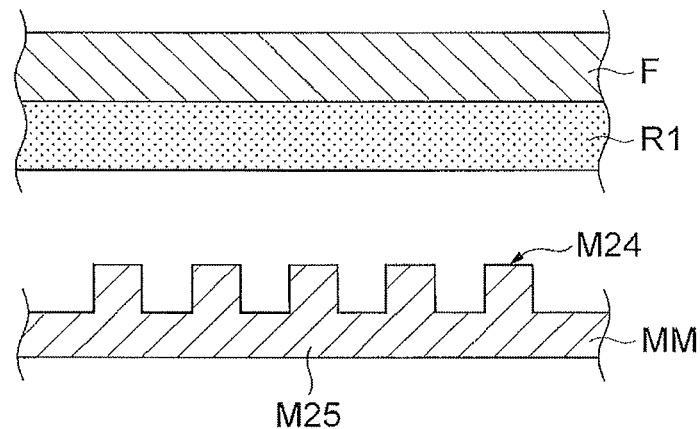
(b) 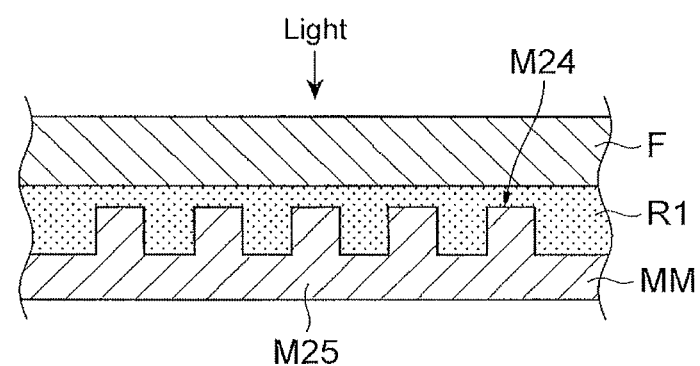
(c) 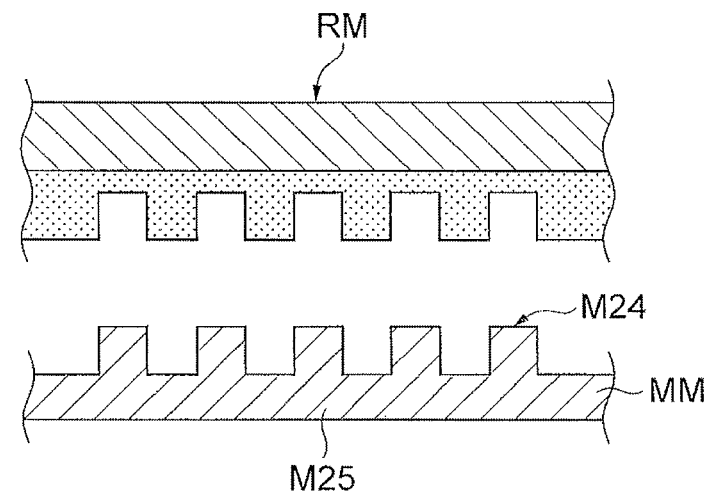

Fig.8
(a) 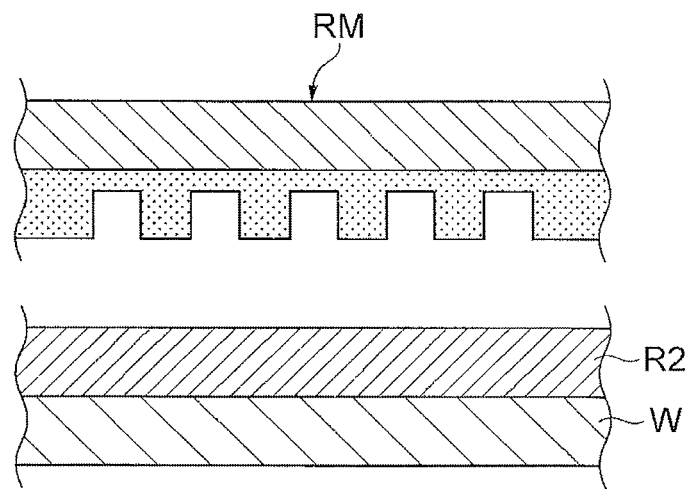
(b) 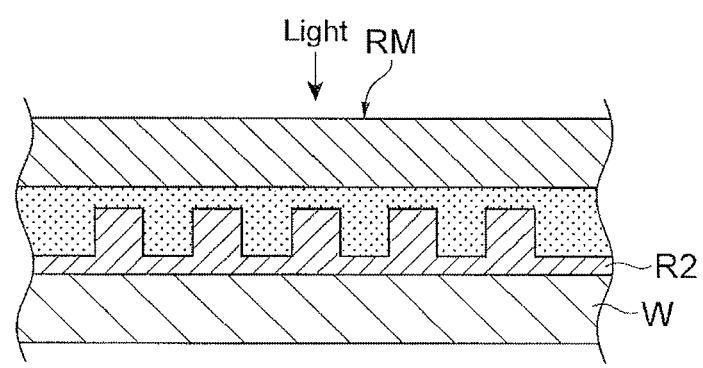
(c) 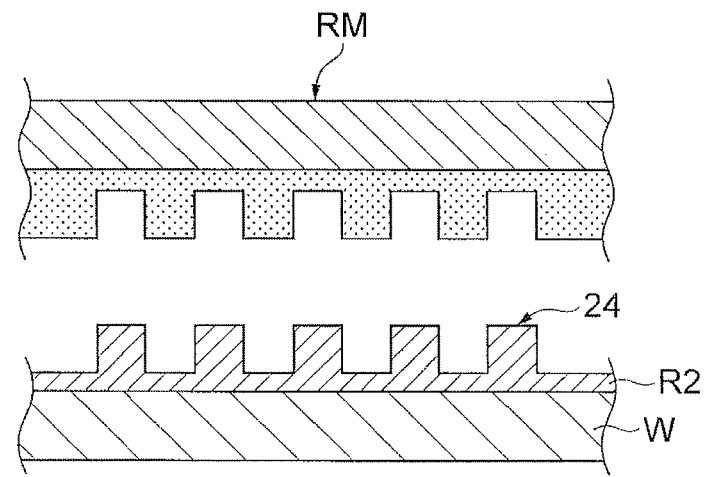

Fig.9
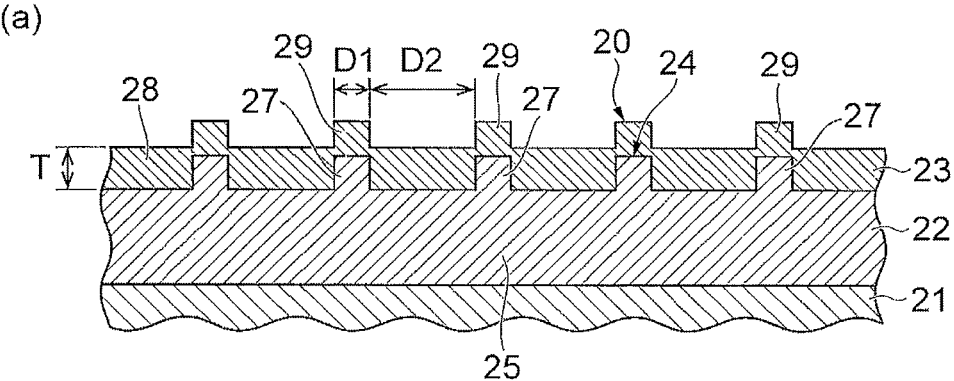
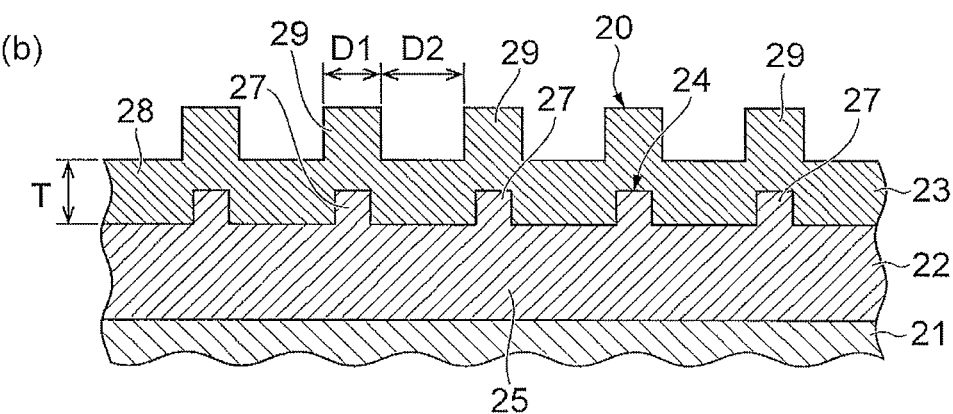
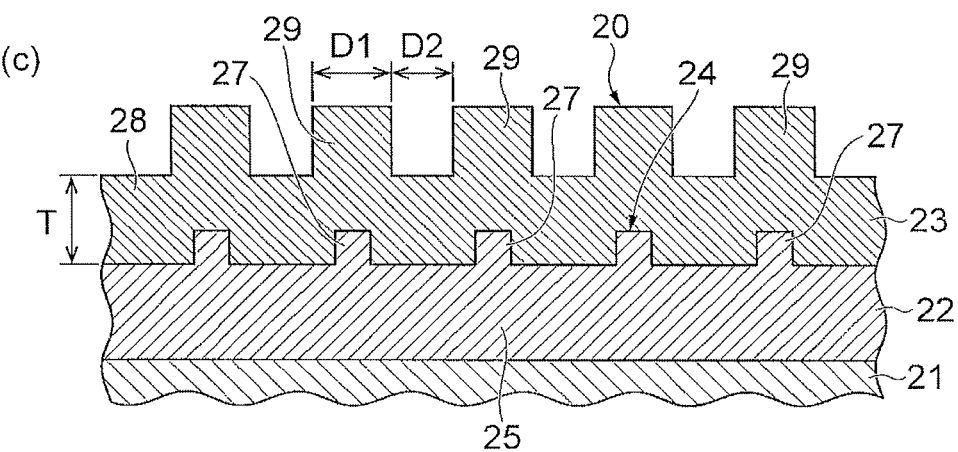

SURFACE-ENHANCED RAMAN SCATTERING ELEMENT, AND METHOD FOR PRODUCING SAME

TECHNICAL FIELD

The present invention relates to a surface-enhanced Raman scattering element and a method for manufacturing the same.

BACKGROUND ART

As a conventional surface-enhanced Raman scattering element, one equipped with a minute metal structure configured to generate surface-enhanced Raman scattering (SERS) has been known (see, for example, Patent Literature 1 and Non. Patent Literature 1). In such a surface-enhanced Raman scattering element, when a sample to be subjected to Raman spectroscopic analysis is brought into contact with the minute metal structure and is irradiated with excitation light in this state, surface-enhanced Raman scattering occurs, whereby Raman scattering light enhanced by about $10^8$ times, for example, is released.

Meanwhile, for example, Patent Literature 2 discloses a minute metal structure in which metal layers are formed on one surface of a substrate and upper surfaces of a plurality of minute projections formed on the one surface of the substrate (or bottom faces of a plurality of fine holes formed on the one surface of the substrate) so as to be out of contact with each other (such that the shortest distance therebetween is on the order of 5 nm to 10 μm).

CITATION LIST

Patent Literature

Patent Literature 1: Japanese Patent Application Laid-Open No. 2011-33518
Patent Literature 2: Japanese Patent Application Laid-Open No. 2009-222507

Non Patent Literature

Non Patent Literature 1: "Q-SERS™ G1 Substrate", [online], Opto Science, Inc., [retrieved from the Internet on 2013 Jul. 5].

SUMMARY OF INVENTION

Technical Problem

When a minute metal structure is formed with a so-called nanogap as mentioned above, electric fields are locally enhanced upon irradiation with excitation light, whereby the intensity of surface-enhanced Raman scattering increases.

In the Raman spectroscopic analysis method disclosed in Patent Literature 1, it is desirable for the minute metal structure exhibiting the SERS effect to be hard to peel from the substrate and have a stable form.

It is therefore an object of the present invention to provide a surface-enhanced Raman scattering element which can increase the intensity of surface-enhanced Raman scattering by a favorable nanogap and a method for manufacturing such a surface-enhanced Raman scattering element.

Solution to Problem

The surface-enhanced Raman scattering element in accordance with one aspect of the present invention comprises a substrate having a principal surface; a fine structure part formed on the principal surface and having a plurality of projections; and a conductor layer formed on the fine structure part and constituting an optical function part for generating surface-enhanced Raman scattering; the conductor layer having a base part formed along the principal surface and a plurality of protrusions protruding from the base part at respective positions corresponding to the projections; the base part having a thickness greater than a height of the projections.

In this surface-enhanced Raman scattering element, the base part of the conductor layer has a thickness greater than the height of projections in the fine structure part. This makes the contact area larger than that in the case with no projections, so that the base part is harder to peel from the fine structure part, whereby the form of the base part is stabilized. Further, since there are no projections of the fine structure part in the parts protruding from the base part in the protrusions of the conductor layer, the protrusions are harder to be affected by deformations in the projections due to thermal expansion and the like, whereby the form of the protrusions is stabilized. As a consequence, a gap formed in the conductor layer by the base part and protrusion favorably functions as a nanogap where electric fields are locally enhanced. Therefore, this surface-enhanced Raman scattering element can increase the intensity of surface-enhanced Raman scattering by a favorable nanogap.

In the surface-enhanced Raman scattering element in accordance with one aspect of the present invention, the projections may be arranged periodically along the principal surface. This configuration can stably increase the intensity of surface-enhanced Raman scattering.

In the surface-enhanced Raman scattering element in accordance with one aspect of the present invention, a plurality of gaps may be formed in the conductor layer by the base part and protrusions so as to surround the respective projections when seen in the projecting direction of the projections. This configuration can increase gaps which favorably function as nanogaps.

The method for manufacturing a surface-enhanced Raman scattering element in accordance with one aspect of the present invention comprises a first step of preparing a substrate having a principal surface formed with a fine structure part having a plurality of projections and a second step of forming a conductor layer on the fine structure part after the first step, the conductor layer constituting an optical function part for generating surface-enhanced Raman scattering, such that the conductor layer has a base part formed along the principal surface and a plurality of protrusions protruding from the base part at respective positions corresponding to the projections; in the second step, the conductor layer is formed by vapor deposition such that the base part has a thickness greater than a height of the projections.

This method for manufacturing a surface-enhanced Raman scattering element can manufacture a surface-enhanced Raman scattering element having a favorable nanogap as mentioned above.

In the method for manufacturing a surface-enhanced Raman scattering element in accordance with one aspect of the present invention, in the second step, a width of the protrusions may be adjusted according to the thickness of the base part. Since the protrusions can be made wider as the base part is thicker, the ratio of the width of the protrusions to the interval between the protrusions adjacent to each other can be set to a desirable value regardless of the pitch of projections in the fine structure part.

Advantageous Effects of Invention

The present invention can provide a surface-enhanced Raman scattering element which can increase the intensity of surface-enhanced Raman scattering by a favorable nanogap and a method for manufacturing such a surface-enhanced Raman scattering element.

BRIEF DESCRIPTION OF DRAWINGS

FIG. 7 is a sectional view illustrating steps of manufacturing the surface-enhanced Raman scattering element of FIG. 5;

FIG. 8 is a sectional view illustrating steps of manufacturing the surface-enhanced Raman scattering element of FIG. 5;

FIG. 9 is a sectional view illustrating steps of manufacturing the surface-enhanced Raman scattering element of FIG. 5;

DESCRIPTION OF EMBODIMENTS

Figure 1:
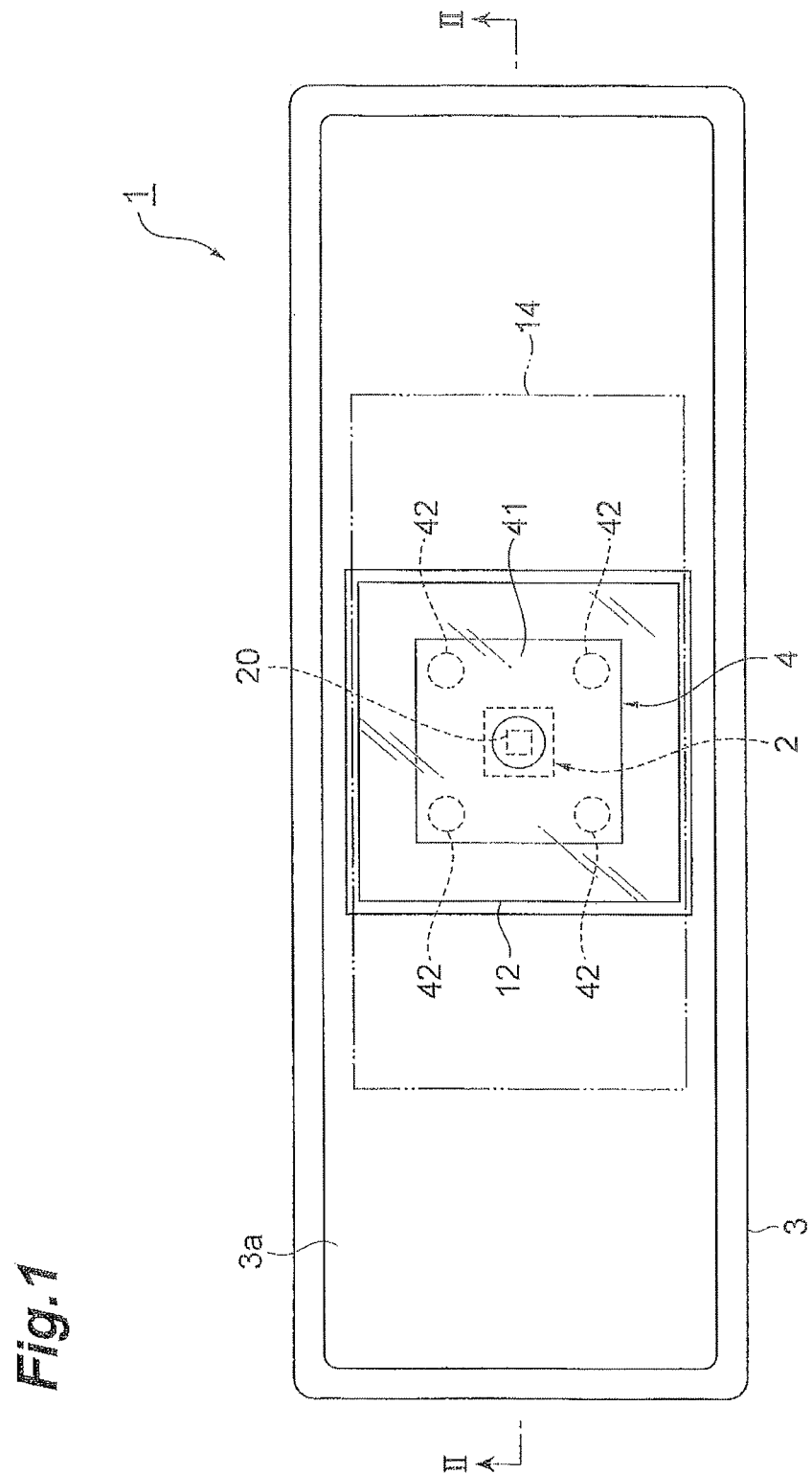
FIG. 1 is a plan view of a surface-enhanced Raman scattering unit employing a surface-enhanced Raman scattering element in accordance with an embodiment of the present invention.

In the following, preferred embodiments of the present invention will be explained in detail with reference to the drawings. In the drawings, the same or equivalent parts will be referred to with the same signs while omitting their overlapping descriptions.

Figure 2:
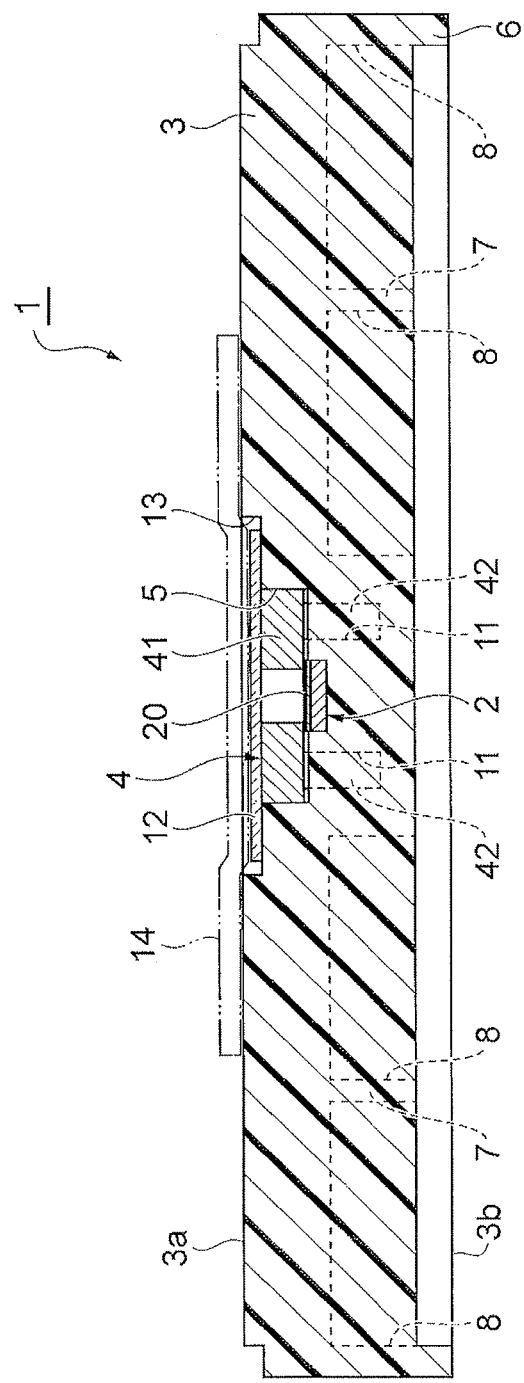
FIG. 2 is a sectional view of the surface-enhanced Raman scattering unit taken along the line II-II of FIG. 1.

As illustrated in FIGS. 1 and 2, a SERS unit (surface-enhanced Raman scattering unit) 1 comprises a SERS element (surface-enhanced Raman scattering element) 2, a measurement board 3 for supporting the SERS element 2 at the time of measurement, and a holding part 4 for mechanically holding the SERS element 2 in the measurement board 3. By "mechanically" is meant "by fitting between members without adhesives and the like."

Figure 3:
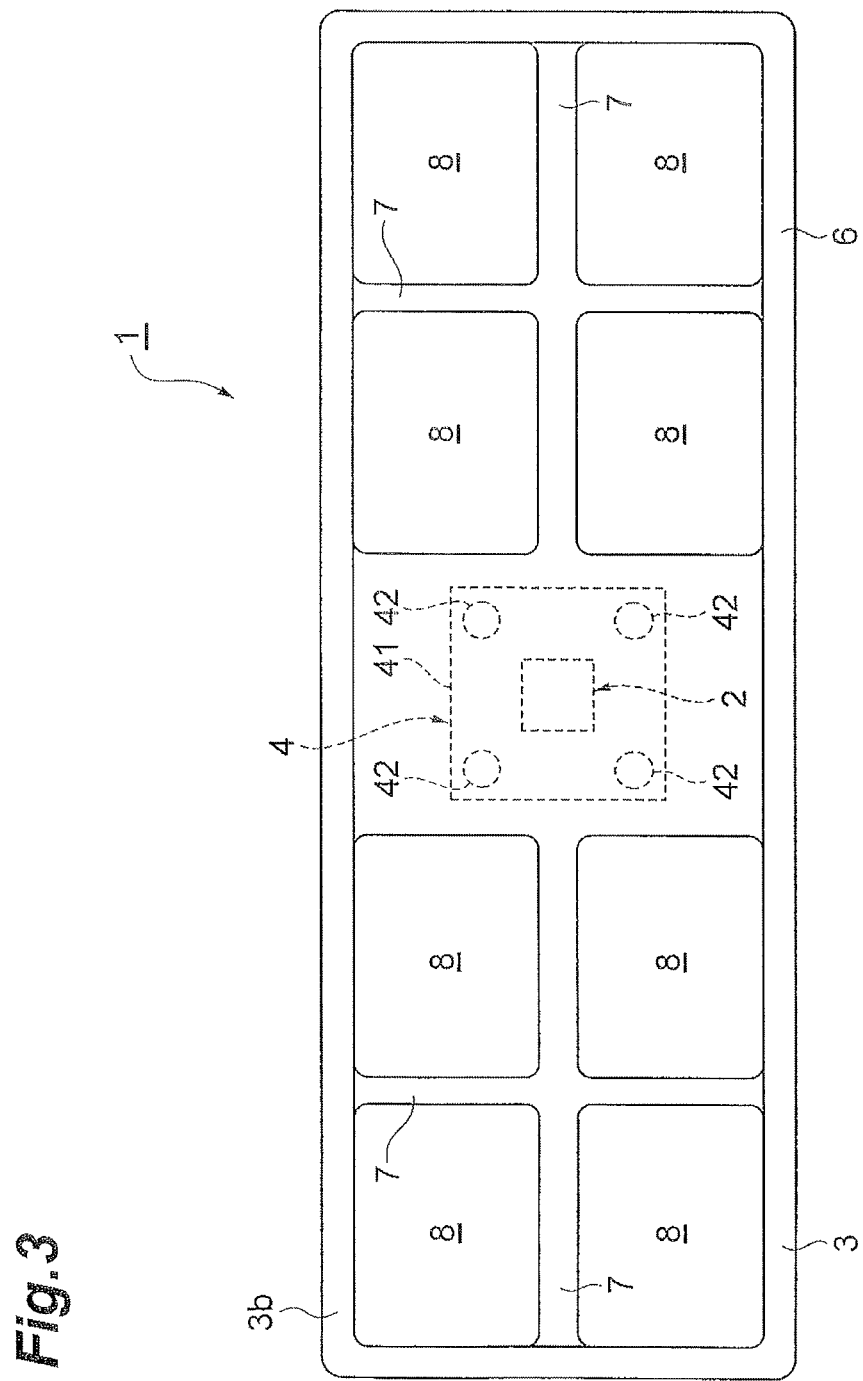
FIG. 3 is a bottom view of the surface-enhanced Raman scattering unit of FIG. 1.

The measurement board 3 has a front face 3a provided with a depression 5 for containing the SERS element 2 and holding part 4. On the other hand, as illustrated in FIGS. 2 and 3, the measurement board 3 has a rear face 3b provided with a plurality of hollowed parts 8 so as to form wall parts 6, 7 extending in directions perpendicular to the thickness direction of the measurement board 3. By way of example, the wall part 6 is formed like a ring along the outer edge of the measurement board 3, while the wall parts 7 are formed like a grid on the inside of the wall part 6. The measurement board 3 is formed into a rectangular plate. The depression 5 and hollowed parts 8 are formed into rectangular parallelepiped shapes. The measurement board 3 like this is integrally formed from a material such as a resin (examples of which include polypropyrene, styrol resin, ABS resin, polyethylene, PET, PMMA, silicone, and liquid crystal polymers), ceramics, glass, or silicon by using a technique such as molding, cutting, or etching.

Figure 4:
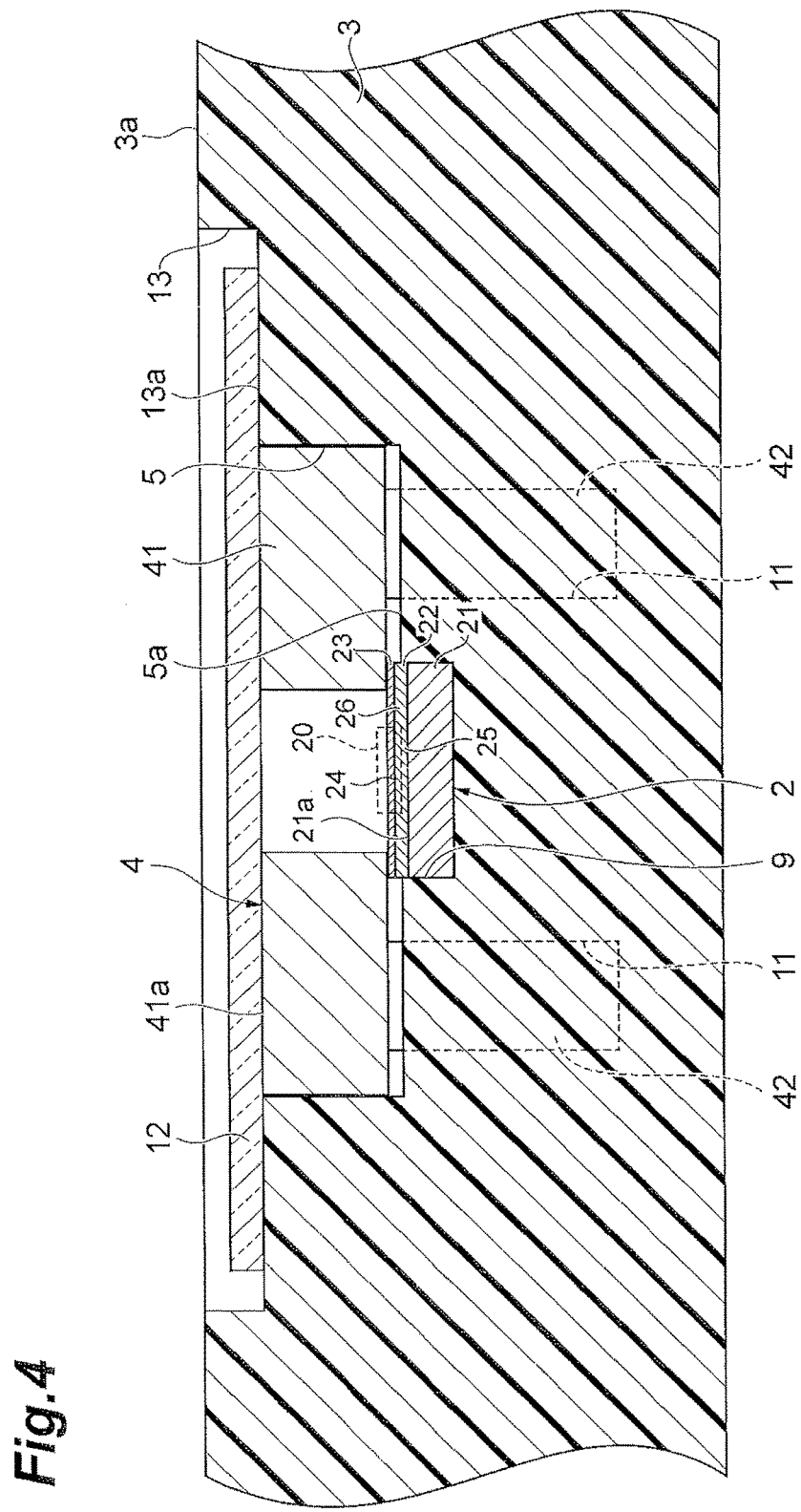
FIG. 4 is a partly enlarged sectional view of the surface-enhanced Raman scattering unit taken along the line of FIG. 1.

As illustrated in FIG. 4, the SERS element 2 comprises a substrate 21, a molded layer 22 formed on the substrate 21, and a conductor layer 23 formed on the molded layer 22. By way of example, the substrate 21 is formed into a rectangular plate by silicon, glass, or the like and has an outer form on the order of several hundred μm×several hundred μm to several ten mm×several ten mm and a thickness on the order of 100 μm to 2 mm.

The molded layer 22 includes a fine structure part 24, a support part 25, and a frame part 26. The fine structure part 24, which is a region having a periodic pattern constructed on a surface layer on the side opposite from the substrate 21 at a center part of the molded layer 22, is formed on a front face (principal surface) 21a of the substrate 21 with the support part 25 interposed therebetween. The support part 25, which is a region supporting the fine structure part 24, is formed on the front face 21a of the substrate 21. The frame part 26, which is a ring-shaped region surrounding the support part 25, is formed on the front face 21a of the substrate 21.

By way of example, the fine structure part 24 has a rectangular outer form on the order of several hundred μm×several hundred μm to several ten mm×several ten mm when seen from one side in the thickness direction of the measurement board 3. In the fine structure part 24, as a periodic pattern, a plurality of pillars, each having a width and height on the order of several nm to several hundred nm, are periodically arranged in the fine structure part 24 at a pitch on the order of several ten nm to several hundred nm along the front face 21a of the substrate 21. The support part 25 and frame part 26 have a thickness on the order of several ten nm to several ten μm. The molded layer 22 like this is integrally formed by molding a resin (examples of which include resins based on acrylics, fluorine, epoxy, silicone, and urethane, PET, polycarbonate, and inorganic/organic hybrid materials) or low-melting glass arranged on the substrate 21 by nanoimprinting, for example.

The conductor layer 23 is integrally formed on the fine structure part 24 and frame part 26. In the fine structure part 24, the conductor layer 23 reaches a surface of the support part 25 which is exposed to the side opposite from the substrate 21. In the SERS element 2, the conductor layer 23 formed on the surface of the fine structure part 24 and on the surface of the support part 25 exposed to the side opposite from the substrate 21 constructs an optical function part 20 which generates surface-enhanced Raman scattering. By way of example, the conductor layer 23 has a thickness on the order of several nm to several μm. The conductor layer 23 like this is formed by vapor-depositing a conductor such as a metal (Au, Ag, Al, Cu, Pt, or the like) on the molded layer 22 molded by nanoimprinting, for example.

The depression 5 has a bottom face 5a provided with a recess 9 which contains a part on the substrate 21 side of the SERS element 2. The recess 9 is formed complementary to a part on the substrate 21 side of the SERS element 2 and restrains the SERS element 2 from moving in directions perpendicular to the thickness direction of the substrate 21. The SERS element 2 is merely in contact with the inner surface of the recess 9 without being secured thereto with adhesives and the like. The recess 9 may contain substantially the whole SERS element 2 so that the front face (surface on the side opposite from the substrate 21) of the conductor layer 23 and the bottom face 5a of the depression 5 are substantially flush with each other.

The holding part 4 has a constraining part 41 formed like a ring so as to surround the optical function part 20 when seen in the thickness direction of the substrate 21 and a plurality of legs 42 extending from the constraining part 41 to the rear face 3b side of the measurement board 3. The bottom face 5a of the depression 5 is formed with fitting holes 11 corresponding to the respective legs 42. The legs 42 are fitted into the respective fitting holes 11 while the constraining part 41 surrounds the optical function part 20 and is in contact with the conductor layer 23 of the SERS element 2. Thus, the holding part 4 formed separately from the measurement board 3 is mechanically secured to the measurement board 3, while the SERS element 2 arranged in the recess 9 is held between the measurement board 3 and the constraining part 41 of the holding part 4. As a consequence, the SERS element 2 is mechanically held against the measurement board 3. The fitting holes 11 have bottoms and do not penetrate through the measurement board 3.

By way of example, the constraining part 41 is formed such as to have a rectangular outer edge and a circular inner edge when seen in the thickness direction of the substrate 21, while the legs 42 extend respectively from four corners of the constraining part 41 to the rear face 3b side of the measurement board 3. The constraining part 41 has the circular inner edge, thereby keeping pressures from locally acting on the SERS element 2. The legs 42 and fitting holes 11 are formed cylindrical. The holding part 4 having the constraining part 41 and legs 42 like these is integrally formed from a material such as a resin (examples of which include polypropylene, styrol resin, ABS resin, polyethylene, PET, PMMA, silicone, and liquid crystal polymers), ceramics, glass, or silicon by using a technique such as molding, cutting, or etching.

The SERS unit 1 further comprises a light-transmitting cover 12. The cover 12 is arranged in a widened part 13 provided in the opening of the depression 5 and shields the opening of the depression 5. The widened part 13 is formed complementary to the cover 12 and restrains the cover 12 from moving in directions perpendicular to the thickness direction of the cover 12. The constraining part 41 of the holding part 4 has a surface 41a substantially flush with a bottom face 13a of the widened part 13. As a consequence, the cover 12 is supported not only by the measurement board 3 but also by the holding part 4. By way of example, the cover 12 is formed into a rectangular plate by glass or the like and has an outer form on the order of 18 mm×1.8 mm and a thickness of about 0.15 mm. As illustrated in FIGS. 1 and 2, a temporary securing film 14 is attached to the SERS unit 1 before used so as to shield the cover 12, thereby preventing the cover 12 from dropping out of the measurement board 3.

Figure 5:
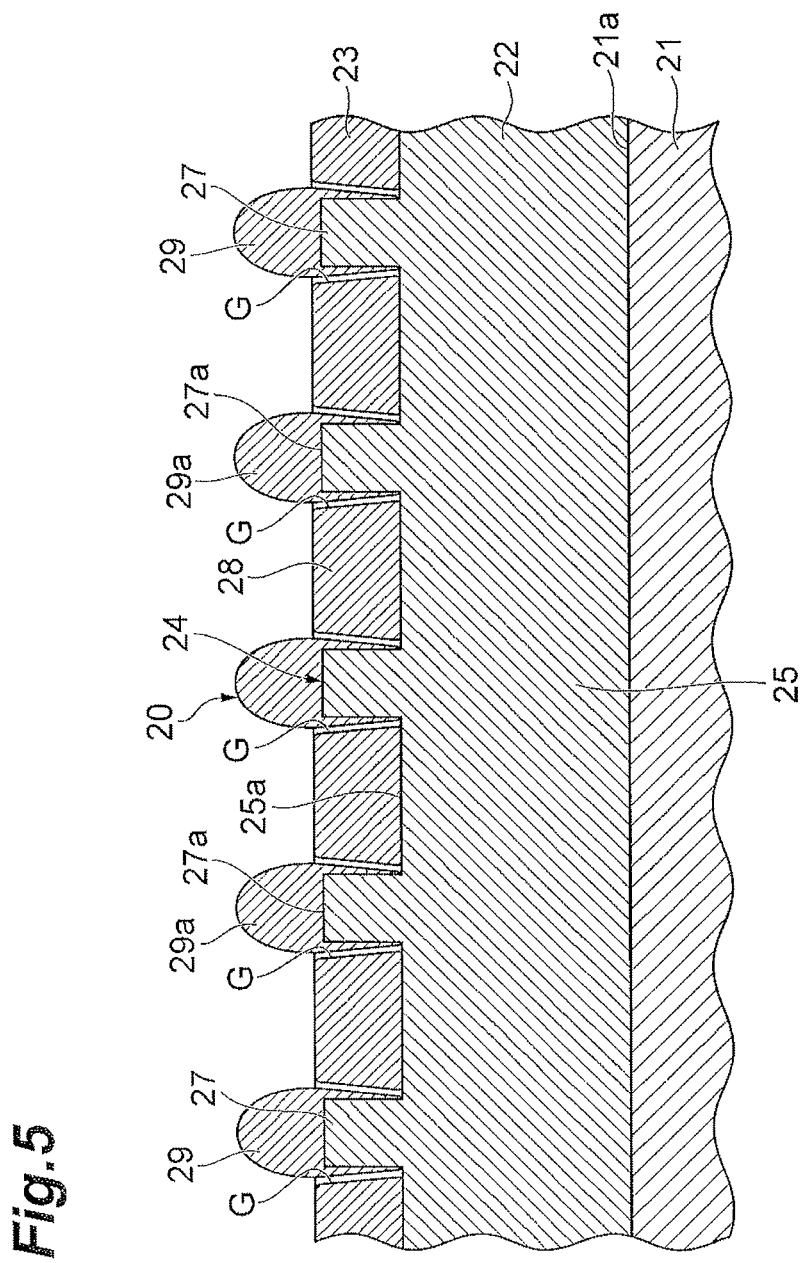
FIG. 5 is a partly enlarged sectional view of the surface-enhanced Raman scattering element in the surface-enhanced Raman scattering unit of FIG. 1.

The structure of the optical function part 20 in the above-mentioned SERS element 2 will be explained in more detail. As illustrated in FIG. 5, the fine structure part 24 has a plurality of pillars (projections) 27 periodically arranged along the front face 21a of the substrate 21. By way of example, the pillars 27, each of which is formed into a circular column having a diameter and height on the order of several nm to several hundred nm, are periodically arranged at a pitch on the order of several ten nm to several hundred nm (preferably 250 nm to 800 nm) along the front face 21a of the substrate 21.

The conductor layer 23 has a base part 28 formed along the front face 21a of the substrate 21 and a plurality of protrusions 29 protruding from the base part 28 at respective positions corresponding to the pillars 27. The base part 28 is formed like a layer on a surface 25a of the support part 25. The base part 28 has a thickness on the order of several nm to several hundred nm, which is greater than the height of the pillars 27. Each protrusion 29 is produced so as to cover its corresponding pillar 27 and has a form constricted at least at an end part on the substrate 21 side. In each protrusion 29, at least an end part 29a on the side opposite from the substrate 21 (i.e., a part located on a top part 27a of the pillar 27) protrudes from the base part 28. For stably forming such a structure, the thickness of the base part 28 is preferably 10 times or less, more preferably 5 times or less, the height of the pillars 27.

In the conductor layer 23, the base part 28 and protrusions 29 form a plurality of gaps G each opening to the side opposite from the substrate 21. Each gap G is formed like a circular ring so as to surround its corresponding pillar 27 when seen in the projecting direction of the pillar 27 (i.e., the thickness direction of the substrate 21). By way of example, the gap G is formed into a trench extending like a circular ring surrounding each pillar 27 when seen in the projecting direction of the pillar 27 and has a width on the order of 0 to several ten nm. The base part 28 and protrusion 29 may be either connected to each other or separated from each other at the deepest part of the gap G.

Figure 6:
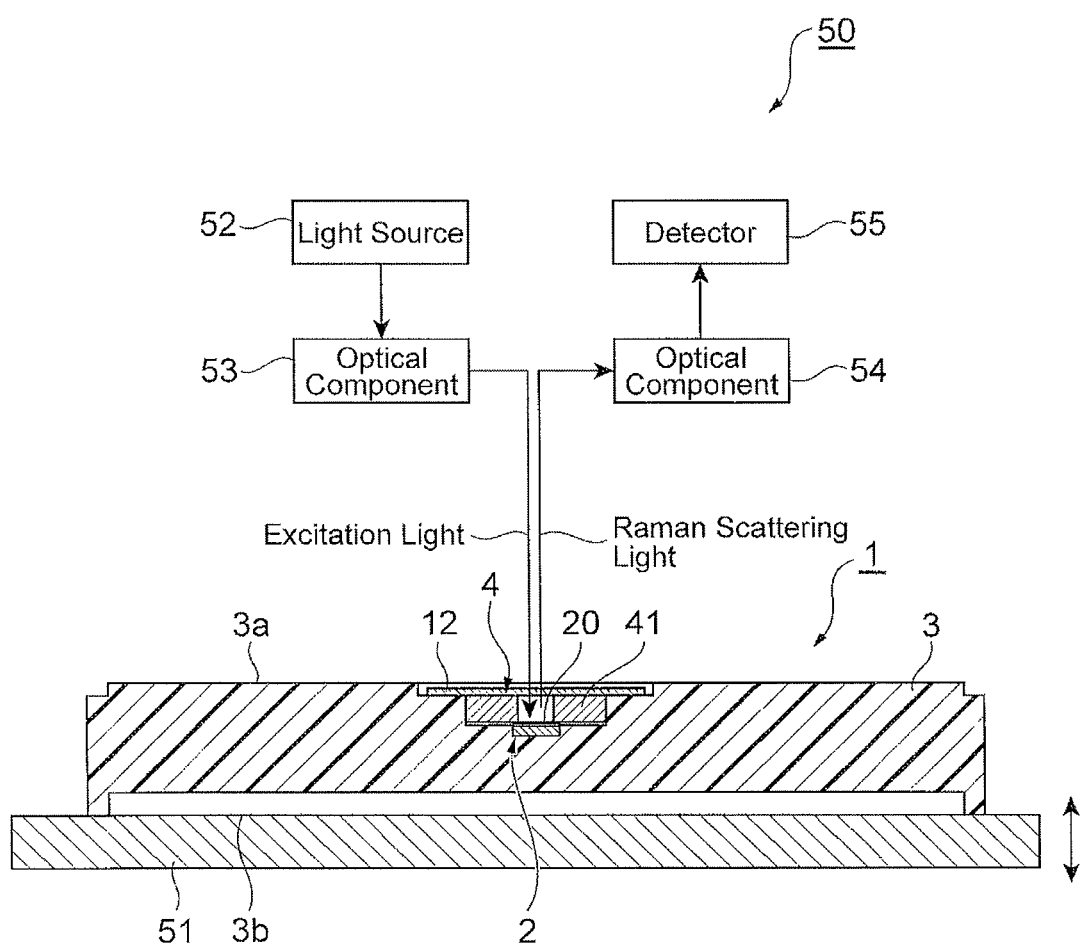
FIG. 6 is a structural diagram of a Raman spectroscopic analyzer in which the surface-enhanced Raman scattering unit of FIG. 1 is set.

A Raman spectroscopic analysis method by the SERS unit 1 constructed as in the foregoing will now be explained. Here, as illustrated in FIG. 6, the Raman spectroscopic analysis method is performed in a Raman spectroscopic analyzer 50 comprising a stage 51 for supporting the SERS unit 1, a light source 52 for emitting excitation light, an optical component 53 for carrying out collimation, filtering, condensing, and the like necessary for irradiating the optical function part 20 with the excitation light, an optical component 54 for carrying out collimation, filtering, and the like necessary for guiding Raman scattering light to a detector 55, and the detector 55 for detecting the Raman scattering light.

First, the SERS unit 1 is prepared, the temporary securing film 14 is peeled from the measurement board 3, and the cover 12 is removed from the measurement board 3. Then, a solution sample (or a dispersion of a powder sample in a solution such as water or ethanol) is dropped to a region on the inside of the constraining part 41 of the holding part 4, so as to arrange the solution sample on the optical function part 20. Subsequently, for reducing the lens effect, the cover 12 is arranged on the widened part 13 of the measurement board 3 and brought into close contact with the solution sample.

Thereafter, the measurement board 3 is arranged on the stage 51, and the SERS unit 1 is set in the Raman spectroscopic analyzer 50. Subsequently, the solution sample arranged on the optical function part 20 is irradiated with the excitation light emitted from the light source 52 through the optical component 53, so as to excite the solution sample. At this time, the stage 51 is moved such that the excitation light has a focal point located at the optical function part 20. This generates surface-enhanced Raman scattering at the interface between the optical function part 20 and solution sample, whereby surface-enhanced Raman scattering light derived from the solution sample is enhanced by about $10^8$ times, for example, and released. The released Raman scattering light is detected by the detector 55 through the optical component 54, whereby Raman spectroscopic analysis is performed.

Not only the above-mentioned method, but the following methods may also be used for arranging the sample on the optical function part 20. For example, while holding the measurement board 3, the SERS element 2 may be dipped in and lifted from the solution sample (or a dispersion of a powder sample in a solution such as water or ethanol), and then the sample may be blown to dry. A minute amount of the solution sample (or a dispersion of a powder sample in a solution such as water or ethanol) may be dropped onto the optical function part 20 and left to dry. A powder sample may be dispersed as it is on the optical function part 20. In these cases, it is not necessary for the cover 12 to be arranged at the time of measurement.

In the SERS element 2, as explained in the foregoing, the thickness of the base part 28 in the conductor layer 23 is greater than the height of the pillars 27 in the fine structure part 24. This makes the contact area larger than that in the case without the pillars 27, so that the base part 28 is harder to peel from the fine structure part 24, whereby the form of the base part 28 is stabilized. Further, since there are no pillars 27 of the fine structure part 24 in the end parts 29a protruding from the base part 28 in the protrusions 29 of the conductor layer 23, the protrusions 29 are harder to be affected by deformations in the pillars 27 due to thermal expansion and the like, whereby the form of the protrusions 29 is stabilized. As a consequence, the gap G formed in the conductor layer 23 by the base part 28 and protrusion 29 favorably functions as a nanogap where electric fields are locally enhanced. Therefore, the SERS element 2 can increase the intensity of surface-enhanced Raman scattering by a favorable nanogap.

In the SERS element 2, the pillars 27 are periodically arranged along the front face 21a of the substrate 21. This can increase the intensity of surface-enhanced Raman scattering.

In the SERS element 2, the gap G is formed so as to surround each pillar 27 when seen in the projecting direction of the pillar 27. This can increase the gaps G favorably functioning as nanogaps.

A method for manufacturing the SERS element 2 will now be explained. First, as illustrated in (a) of FIG. 7, a film base F is prepared, and a UV-curable resin is applied to a surface of the film base F, so as to form a UV-curable resin layer R1 on the film base F. On the other hand, a master mold MM is prepared. The master mold MM includes a fine structure part M24 corresponding to the fine structure part 24 and a support part M25 for supporting the fine structure part M24. On the support part M25, a plurality of fine structure parts M24 are arranged in a matrix. The fine structure parts M24 are surface-treated with a releasing agent or the like so as to be released easily at a later step.

Next, as illustrated in (b) of FIG. 7, the master mold MM is pressed against the UV-curable resin layer R1 on the film base F, and the UV-curable resin R1 is irradiated with UV in this state, so as to be cured, whereby a pattern of the plurality of fine structure parts M24 is transferred to the UV-curable resin R1. Then, as illustrated in (c) of FIG. 7, the master mold MM is released from the UV-curable resin R1 on the film base F, so as to yield a replica mold (replica film) RM having the pattern of the plurality of fine structure parts M24 transferred thereto.

Subsequently, as illustrated in (a) of FIG. 8, a silicon wafer W to become the substrate 21 is prepared, and a UV-curable resin is applied to a surface of the silicon wafer W, so as to form a nanoimprinting layer R2 to become the molded layer 22 on the silicon wafer W. Then, as illustrated in (b) of FIG. 8, the replica mold RM is pressed against the nanoimprinting layer R2 on the silicon wafer W, and the nanoimprinting layer R2 is irradiated with UV in this state, so as to be cured, whereby a pattern of the replica mold RM is transferred to the nanoimprinting layer R2. Thereafter, as illustrated in (c) of FIG. 8, the replica mold RM is released from the nanoimprinting layer R2 on the silicon wafer W, so as to yield the silicon wafer W formed with a plurality of fine structure parts 24.

The substrate 21 formed with the fine structure part 25 as in the foregoing is prepared on a wafer level (first step), and a film of a metal such as Au or Ag is produced on the molded layer 22 by evaporation method, so as to form the conductor layer 23 constituting the optical function part 20 on the fine structure part 24 (second step). At this time, a metal layer such as Au or Ag is formed by vapor deposition such that the base part 28 in the conductor layer 23 has a thickness greater than the height of the pillars 27 in the fine structure part 24. Subsequently, the silicon wafer W is cut for each fine structure part 24 (i.e., for each optical function part 20), whereby a plurality of SERS elements 2 are obtained. Here, the metal layer may be formed by vapor deposition after cutting the silicon wafer W into chips.

The fine structure part 24 may be formed on the substrate 21 by thermal nanoimprinting or etching using a mask having a two-dimensional pattern formed by photoetching, electron beam lithography, or the like instead of the above-mentioned nanoimprinting. For forming the conductor layer 23, a conductor layer such as a metal may be formed by vapor deposition methods (sputtering, CVD, and the like) other than the evaporation method.

As explained in the foregoing, the method for manufacturing the SERS element 2 can form the conductor layer 23 with the nano-order gaps G with a favorable reproducibility in a simple process, thereby enabling mass production of the SERS element 2.

As illustrated in FIG. 9, the width (outer diameter) D1 of the protrusion 29 may be adjusted according to the thickness T of the base part 28 when forming the conductor layer 23. Since the width D1 of the protrusion 29 can be made larger as the thickness T of the base part 28 is greater, the ratio (duty ratio) D1/(D1+D2) of the width D1 of the protrusion 29 to the interval D2 between the protrusions 29 adjacent to each other can be set to a desirable value regardless of the pitch P of pillars 27 in the fine structure part 24.

Figure 10:
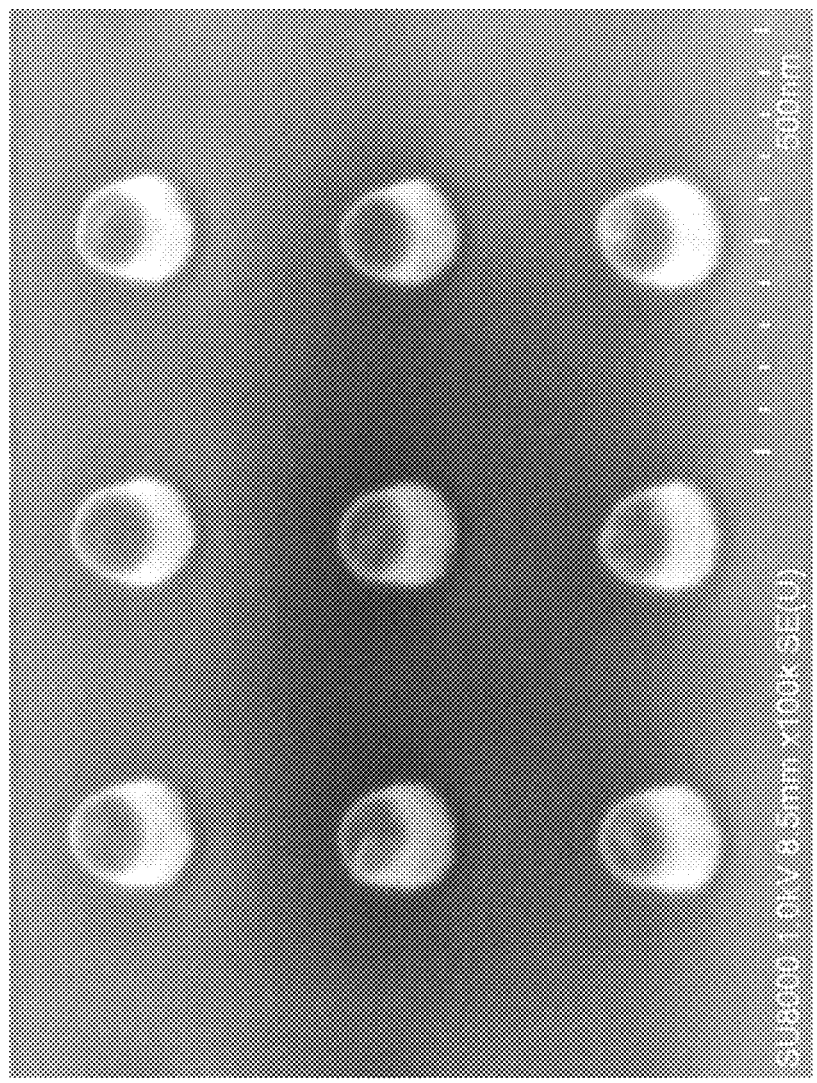
FIG. 10 is a SEM photograph of a fine structure part in the surface-enhanced Raman scattering element of Example 1.
Figure 11:
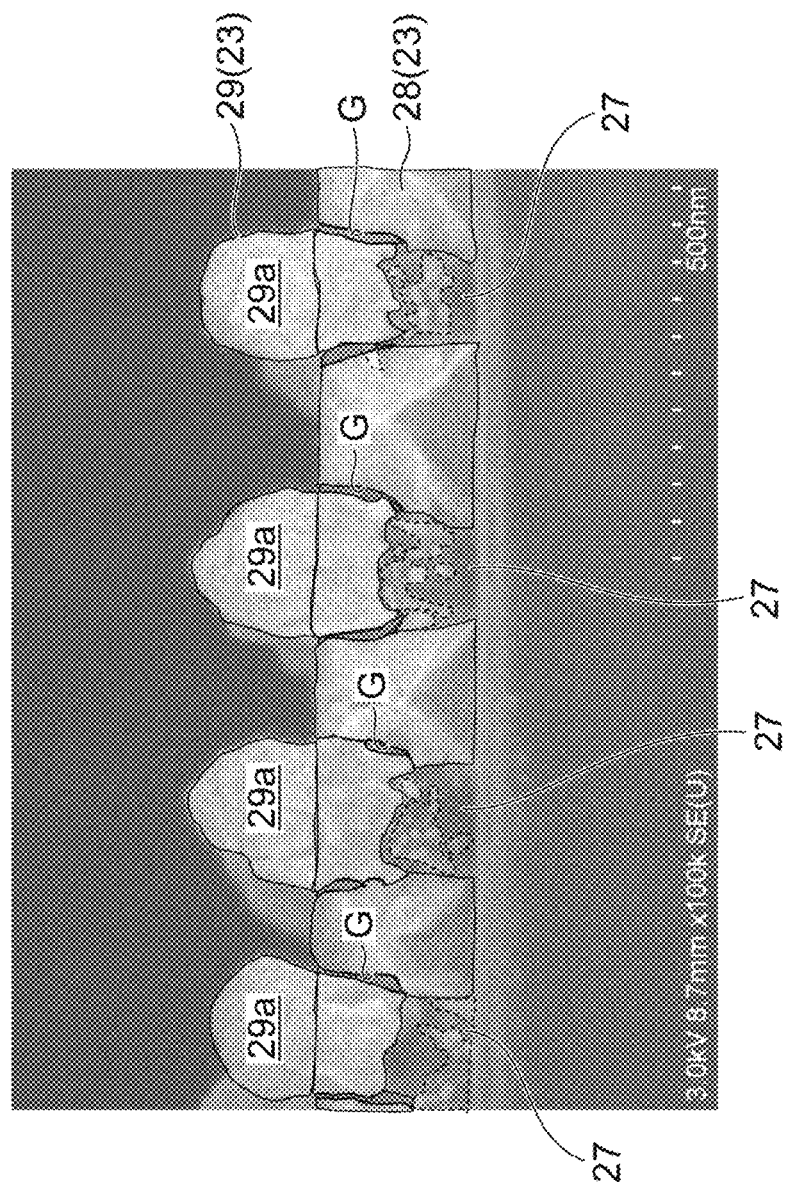
FIG. 11 is a SEM photograph of a cross section of an optical function part in the surface-enhanced Raman scattering element of Example 1.

Examples of the SERS element will now be explained. FIG. 10 is a SEM photograph of a fine structure part in the SERS element of Example 1. In the fine structure part in the SERS element of Example 1, pillars, each shaped into a truncated cone having a width of 90 nm to 150 nm and a height of 150 nm, are periodically arranged at a pitch of 360 nm along the front face of the substrate. On this fine structure part, Au was vapor-deposited as a conductor layer with a thickness of 200 nm. FIG. 11 is a SEM photograph of a cross section of an optical function part in the SERS element of Example 1 (a SEM photograph capturing the optical function part in a direction perpendicular to the front face of the substrate). In Example 1, the SERS element was broken into two, and the resulting cross section was observed with SEM. As illustrated in FIG. 11, together with the pillars 27 and the base part 28 and protrusions 29 (including the end parts 29a protruding from the base part 28) of the conductor layer 23, a number of gaps G favorably functioning as nanogaps are seen about the protrusions 29 in the SERS element of Example 1.

Figure 12:
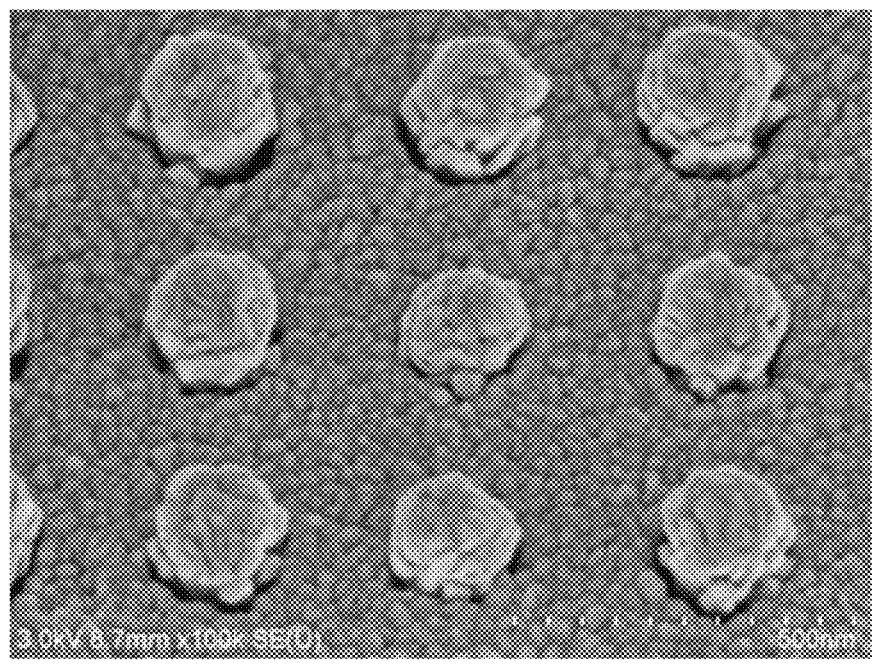
FIG. 12 is a SEM photograph of an optical function part in the surface-enhanced Raman scattering element of Example 2.

FIG. 12 is a SEM photograph of an optical function part in the SERS element of Example 2 (a SEM photograph capturing the optical function part in a direction tilted by 30° from a direction perpendicular to the surface of the substrate). In Example 2, Au was vapor-deposited as a conductor layer with a thickness of 200 nm. As illustrated in FIG. 12, a number of gaps favorably functioning as nanogaps are also seen about the protrusions in the SERS element of Example 2.

The following is a specific method for making the SERS element of Example 2. First, using a mold in which holes, each having a hole diameter of 120 nm and a hole depth of 180 nm, were arranged in a square lattice at a hole interval (distance between center lines of holes adjacent to each other) of 360 nm, a resin on a substrate made of glass was molded by nanoimprinting, so as to produce a fine structure part. In thus produced fine structure part, the pillars had a diameter of 120 nm, a height of 150 nm, and a pillar pitch (distance between center lines of pillars adjacent to each other) of 360 nm.

Next, a film of Au was formed as a conductor layer by resistance heating vacuum vapor deposition on the produced fine structure part, so as to yield the SERS element of Example 2. The film forming condition for the conductor layer was "film thickness: as mentioned above; evaporation method rate: 0.02 nm/s; degree of vacuum during film forming: $1.5 \times 10^{-5}$ torr; substrate rotation: none; substrate temperature control: none." For improving the adhesion of the conductor layer, a film of Ti may be formed as a buffer layer by resistance heating vacuum vapor deposition on the produced fine structure part, and a film of Au may be formed as a conductor layer by resistance heating vacuum vapor deposition on the buffer layer.

Figure 13:
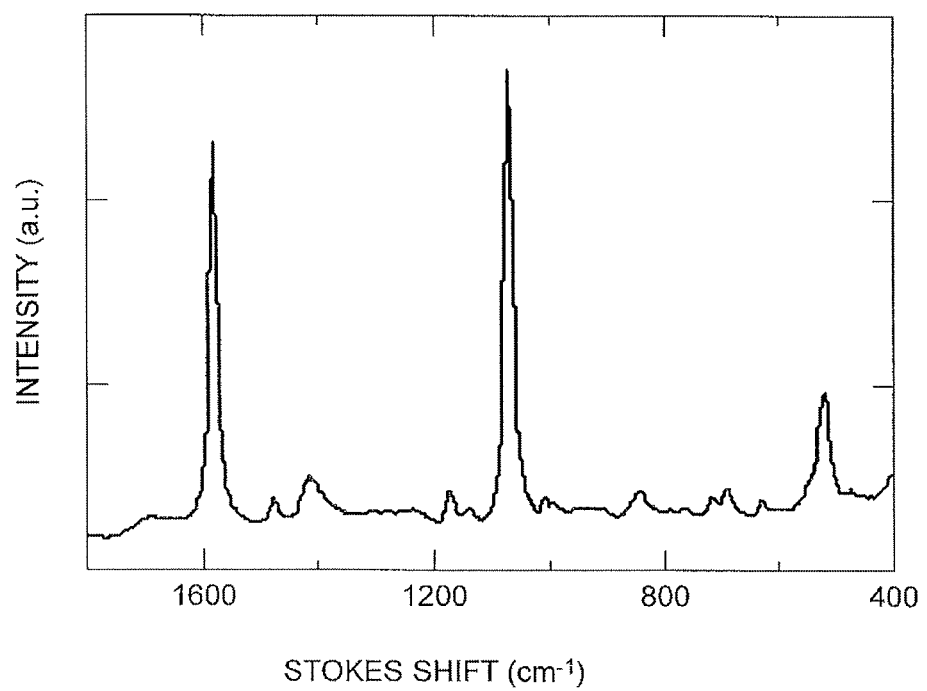
FIG. 13 is a graph illustrating a relationship between Stokes shift and signal intensity concerning the surface-enhanced Raman scattering element of Example 2.

FIG. 13 is a graph illustrating a relationship between Stokes shift and signal intensity concerning the surface-enhanced Raman scattering element of Example 2. Here, the SERS element of Example 2 was dipped in an ethanol solution of mercaptobenzonic acid (1 mM) for two hours, then rinsed with ethanol, and dried with a nitrogen gas, so that a sample was arranged on the optical function part of the SERS element. The sample was subjected to Raman spectrometry with excitation light having a wavelength of 785 nm. This resulted in a SERS spectrum of mercaptobenzonic acid as illustrated in FIG. 13.

While an embodiment of the present invention is explained in the foregoing, the present invention is not limited to the above-mentioned embodiment. For example, the arrangement structure of the pillars 27 may be one dimensional instead of two dimensional, a triangle lattice instead of a square lattice, or non-periodic. The cross-sectional form of the pillars 27 is not limited to circles, but may be ellipses or polygons such as triangles and quadrangles. The gap G may also be formed so as to surround the pillar 27 in ring forms (such as ellipses) other than circles. The gap G may not be formed so as to surround the pillar 27 continuously but intermittently in a state divided into a plurality of regions. Thus, without being restricted to those mentioned above, various materials and forms can be employed for constituents of the SERS element 2.

When attention is focused on a pair of projections (those corresponding to the pillars 27) adjacent to each other, the width of the gap formed by the base part and protrusion is smaller than the distance between the conductor layer formed on the outer surface of one projection and that formed on the outer surface of the other projection. This can easily and stably form such a narrow gap (gap favorably functioning as a nanogap) as to be unattainable by the configuration of the fine structure part alone.

The fine structure part 24 may be formed on the front face 21a of the substrate 21 either indirectly with the support part 25, for example, interposed therebetween as in the above-mentioned embodiment or directly. The conductor layer 23 may be formed on the fine structure part 24 either indirectly with a layer such as a buffer metal (Ti, Cr, or the like) for improving the adhesion of a metal to the fine structure part 24, for example, interposed therebetween or directly.

INDUSTRIAL APPLICABILITY

The present invention can provide a surface-enhanced Raman scattering element which can increase the intensity of surface-enhanced Raman scattering by a favorable nanogap, and a method for manufacturing such a surface-enhanced Raman scattering element.

REFERENCE SIGNS LIST

2: SERS element (surface-enhanced Raman scattering element); 20: optical function part; 21: substrate; 21a: front face (principal surface); 23: conductor layer; 24: fine structure part; 27: pillar (projection); 28: base part; 29: protrusion; G: gap.

The invention claimed is:

1. A surface-enhanced Raman scattering element comprising:
   a substrate having a principal surface;
   a fine structure part formed on the principal surface and having a plurality of projections; and
   a conductor layer formed on the fine structure part and constituting an optical function part for generating surface-enhanced Raman scattering;
   wherein the conductor layer has a base part formed along the principal surface and a plurality of protrusions protruding from the base part at respective positions corresponding to the projections; and
   wherein the base part has a thickness greater than a height of the projections,
   the projections are pillars, and
   a gap that opens at an upper face of the base part positioned higher than a top part of a pillar and extends downward to a position lower than the top part of the pillar, the gap being formed between the base part and a protrusion.

2. A surface-enhanced Raman scattering element according to claim 1, wherein the projections are arranged periodically along the principal surface.

3. A surface-enhanced Raman scattering element according to claim 1, wherein a plurality of gaps are formed in the conductor layer between the base part and protrusions so as to surround the respective projections when seen in the projecting direction of the projections, the projecting direction being the thickness direction of the substrate.

4. A method for manufacturing a surface-enhanced Raman scattering element, the method comprising:

a first step of preparing a substrate having a principal surface formed with a fine structure part having a plurality of projections; and a second step of forming a conductor layer on the fine structure part after the first step, the conductor layer constituting an optical function part for generating surface-enhanced Raman scattering, such that the conductor layer has a base part formed along the principal surface and a plurality of protrusions protruding from the base part at respective positions corresponding to the projections, wherein, in the second step, the conductor layer is formed by vapor deposition such that the base part has a thickness greater than a height of the projections, the projections are pillars, and the method further comprising forming a gap that opens at an upper face of the base part positioned higher than a top part of a pillar and extends downward to a position lower than the top part of the pillar, the gap being formed between the base part and a protrusion.

5. A method for manufacturing a surface-enhanced Raman scattering element according to claim 4, wherein, in the second step, a width of the respective protrusions is adjusted according to the thickness of the base part.

* * * * *